United States Patent [19]

Chamberlin, Sr.

[11] Plant 4,980

[45] Feb. 8, 1983

[54] PEACH TREE

[75] Inventor: Thomas O. Chamberlin, Sr., Visalia, Calif.

[73] Assignee: H. P. Metzler & Sons, Inc., Del Rey, Calif.

[21] Appl. No.: 292,694

[22] Filed: Aug. 13, 1981

[51] Int. Cl.[3] ..... A01H 5/03

[52] U.S. Cl. ..... Plt./43

[58] Field of Search ..... Plt./43

*Primary Examiner*—Robert E. Bagwill
*Attorney, Agent, or Firm*—Huebner & Worrel

[57] ABSTRACT

A peach tree with yellow flesh of very smooth and tight texture ripening very evenly throughout approximately six days after the unpatented Springcrest Peach Tree.

1 Drawing Figure

BACKGROUND OF THE VARIETY

The present invention relates to a new and distinct variety of peach tree broadly characterized by its yellow flesh which is of a very smooth and tight texture and having a very smooth taste with very little acidity and more particularly to such a peach tree wherein the fruit is of a semi-freestone type ripening approximately six days after the Springcrest variety and having excellent shipping and keeping quality.

Among the attributes which are important in the commercialization of tree fruit, and particularly with respect to peaches, are early ripening, attractive appearance, size and color and good keeping and shipping quality. Each plays an important part in insuring a good market acceptance for the fruit. The fruit of the unpatented Springcrest peach tree has achieved an excellent market acceptance and has good attributes in the foregoing respects which have contributed to this success. The fruit of the present variety ripens about six days after the Springcrest peach and has excellent attributes in these same respects, but has superior ripening characteristics which facilitate handling of the fruit and has superior keeping and shipping quality.

ORIGIN AND ASEXUAL REPRODUCTION OF THE NEW VARIETY

The instant new variety of peach tree was discovered by myself in 1976 and is a newly found seedling of the June Lady peach tree. Seeds of the June Lady were planted in a plot in the nursery of H. P. Metzler & Sons, Inc. at 5286 South Del Rey Avenue, Del Rey, Calif. 93616 in 1974. The first fruit of the present variety was observed in June, 1976 and its superior characteristics discovered at that time. The present variety was asexually propagated under my direction at H. P. Metzler & Sons, Inc. in 1976 by grafting several seedlings with scions from the newly discovered seedling and then moving them to a test nursery on Ranch No. 18 of H. P. Metzler & Sons, Inc. at Del Rey, Calif. Subsequently 125 seedlings were budded from the new variety and planted in the test plot. The seedlings of the new variety were observed in 1978 and 1979 under field conditions and the fruit and tree characteristics resulting from such asexual reproduction proved to be identical to those of the original seedling of the new variety.

SUMMARY OF THE NEW VARIETY

The instant variety of peach tree is characterized by its bright yellow flesh sometimes tinged with reddish orange areas, ripening approximately six days after the Springcrest peach tree under the growing conditions prevailing in the San Joaquin Valley of California. The fruit is of the semi-freestone type with flesh of a very smooth and tight texture and possessing a smooth taste with very little acidity. There has been a noticeable absence of splitting of the stone or pit of the fruit. The fruit is further characterized by ripening evenly in such a manner that the apex does not soften before the base is ripe which permits the fruit to be left on the tree until approximately 90 percent of the fruit is ripe. Where this is done, the entire crop can be picked in one operation thereby achieving substantial saving in the picking and packing of the fruit. Fruit is still further characterized by having very good keeping and shipping quality permitting the fruit to be kept in refrigerated storage for from four to five weeks without noticeable damage or loss in color, flavor or texture.

BRIEF DESCRIPTION OF THE DRAWING

The accompanying drawing is a color photograph of four mature fruit of the instant variety, one positioned to show the apex, a second positioned to show the stem, a third positioned to show the side and a fourth sliced along the suture plane to expose the flesh and with the flesh having been cleaned from the stone to expose its appearance. A representative twig is also shown in the photograph with characteristic leaves.

DETAILED DESCRIPTION

Referring more specifically to the pomological details of this new and distinct variety of peach tree, the following characteristics were observed under the ecological conditions prevailing at the nursery of H. P. Metzler & Sons, Inc. at Del Rey, Fresno County, Calif. and is an outlined description thereof. All major color code plate identifications are by reference to the Color Name Chart of the Inter-Society Color Council, National Bureau of Standards.

TREE

Size: Normal size and vigor with a normal form subject to variation by pruning methods.

Productivity: Regular and good bearing.

Trunk: Normal size with medium size lenticels and semi-smooth surface.

Branches: Normal size with semi-smooth surface of the same character as the trunk and medium size lenticels.

Leaves: Normal size.

*Length.*—About 7 inches [17.78 CM].

*Width.*—1¼ inches [3.175 CM] to 1⅜ inches [3.4925 CM].

*Texture.*—Smooth.

*Shape.*—Lanceolate with apex acuminate.

*Margin.*—Crenate.

*Petiole.*—About 9/32 inch [0.714375 CM] in length and 1/16 inch [0.15875 CM] thick.

*Glands.*—Reniform, with two opposed at base of leaf; color, yellow green (116 Brill Y-G).

*Color.*—Green (#125 M. O1G).

Flower buds: Small and round.

*Length.*—¼ inch [0.635 CM] before petal opening.

*Width.*—3/16 inch [0.47625 CM] in diameter with stamen showing, but before petal opening.

Flowers:

*Dates of bloom.*—March 5th to March 8th.

*Size.*—Small, each petal 5/16 inch [0.79375 CM] in length when open.

*Color.*—Dark pink in general color, outer edge of petal (2.S pink) and center of flower (4.1 pink).

*Pollen.*—Present.

FRUIT

Maturity: Reached in the San Joaquin Valley of California about May 30 to June 6, or about 6 days after Springcrest peach tree.

Size: Varies with thinning, but generally 2 3/16 inches [5.55625 CM] to 2¾ inches [6.985 CM] in diameter.

Form: Uniform and symmetrical.

*Suture.*—Very smooth extending from the base to the apex.

*Stem cavity.*—Rounded and ¼ inch [0.635 CM] in depth.

*Apex.*—Smooth to very slight depression, but in some seasons a very slight apex point.

Skin:

*Thickness.*—Medium.

*Texture.*—Tough and tenacious to flesh.

*Tendency to crack.*—None.

*Pubescense.*—Very light.

*Color.*—Dark red (14 V deep red) to bright red (13 deep red) with some yellow (0.82 V yellow).

Flesh:

*Color.*—Flesh is bright yellow (82 V yellow).

*Juice.*—Moderate.

*Texture.*—Very smooth and tight and of the non-melting type.

*Ripening.*—Ripen quite evenly in that apex does not get soft before base is ripe. Texture is even throughout the fruit.

*Flavor.*—Mild.

*Aroma.*—Slight.

*Fibers.*—None.

*Eating quality.*—Good.

Stone:

*Type.*—Semi-freestone while ripening. After ripening most of flesh will come free from pit.

*Size.*—1¼ inches [3.175 CM] in length and 1 inch [2.54 CM] in diameter.

*Shape.*—Generally oval. Ridges generally in longitudinal line about 1/16 inch [0.15875 CM] in depth. Seed, normal in shape with narrow stem base and pointed apex with one side narrow and with wider semi-flat base.

*Color.*—Whitish (92 Y White).

*Splitting tendency.*—None.

Use: Fresh market.

*Keeping quality.*—Very good. Fruit has been kept in storage as long as four to five weeks without noticeable deterioration.

*Shipping quality.*—Very good.

Although the new variety of peach tree possesses the described characteristics as a result of the growing conditions in Fresno County, Calif., in the Central portion of the San Joaquin Valley, it is to be understood that variations of the usual magnitude and characteristics incident to growing conditions, fertilization, pruning, pest control and other horticultural practices are to be expected.

Having thus described and illustrated my new variety of peach tree, what is claimed as new and desired to be secured by Letters Patent is:

1. A new and distinct variety of peach tree substantially as illustrated and described and which is characterized by regular and good bearing of early ripening, medium size, semi-freestone, yellow-fleshed fruit having flesh of a very smooth and tight texture ripening quite evenly throughout the fruit in that the apex normally does not soften before the base of the fruit is ripe; and ripening about 6 days after the unpatented Springcrest peach tree.

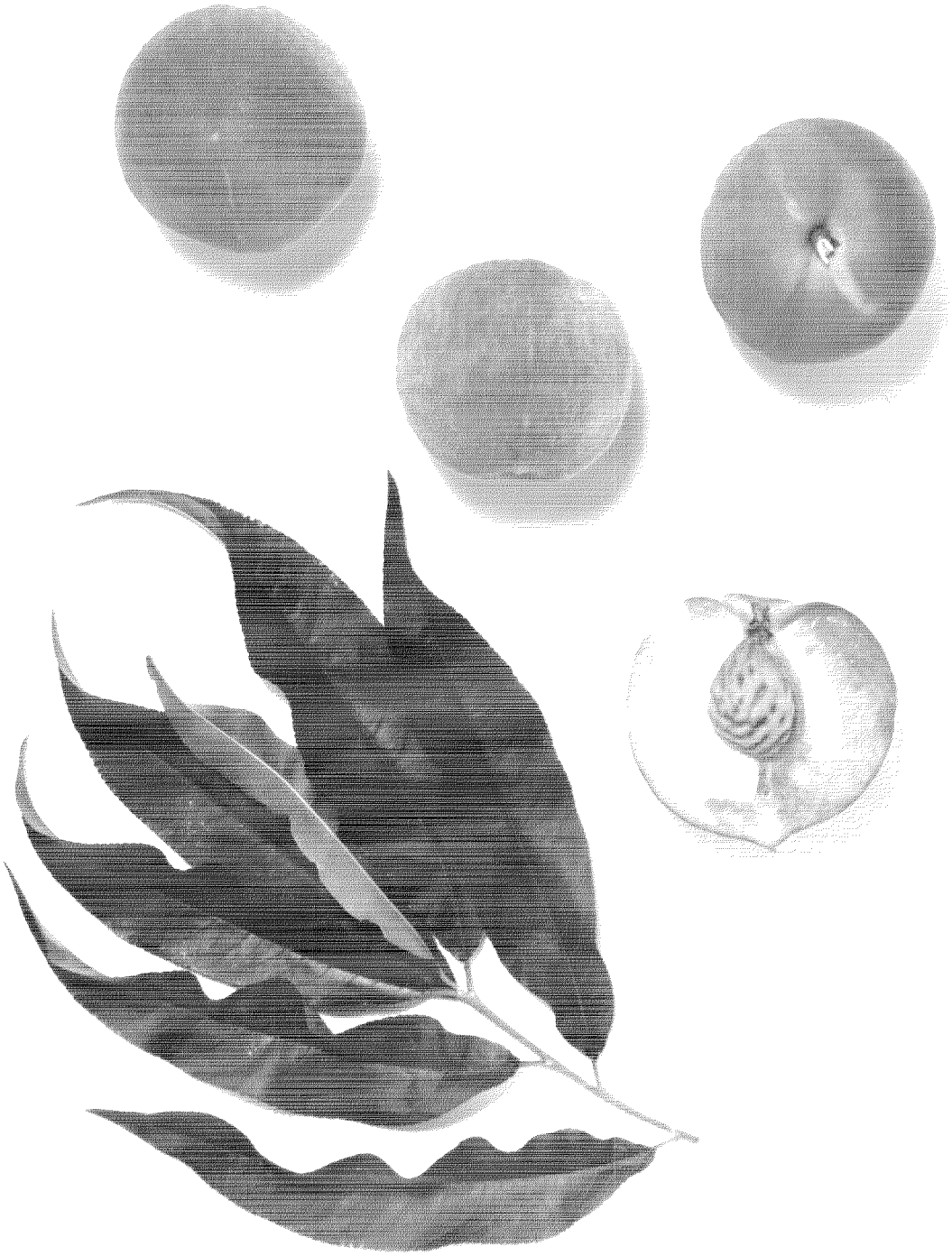

* * * * *